United States Patent [19]

Sasaki et al.

[11] 4,330,429

[45] May 18, 1982

[54] PROCESS FOR REGENERATING AN ANTIMONY CONTAINING OXIDE CATALYST

[75] Inventors: Yutaka Sasaki; Hiroshi Utsumi; Akimitsu Morii, all of Yokohama; Yoshimi Nakamura, Kawasaki, all of Japan

[73] Assignee: Nitto Chemical Industry Co., Ltd., Tokyo, Japan

[21] Appl. No.: 203,754

[22] Filed: Nov. 3, 1980

Related U.S. Application Data

[63] Continuation of Ser. No. 959,810, Nov. 13, 1978, abandoned.

[30] Foreign Application Priority Data

Nov. 12, 1977 [JP] Japan .............................. 52/135235

[51] Int. Cl.$^3$ ..................... B01J 23/92; C07C 120/14; C07C 5/48; C07C 11/12
[52] U.S. Cl. .................................. 252/413; 252/412; 260/465.3; 585/626
[58] Field of Search ................................ 252/413, 412

[56] References Cited

U.S. PATENT DOCUMENTS

| | | | |
|---|---|---|---|
| 3,152,170 | 10/1964 | Barclay et al. | 252/456 |
| 3,200,081 | 8/1965 | Callahan et al. | 252/443 |
| 3,308,151 | 3/1967 | Callahan et al. | 252/456 |
| 3,346,513 | 10/1967 | Hadley | 585/626 |
| 3,668,147 | 6/1972 | Yoshino et al. | 252/439 |
| 4,049,575 | 9/1977 | Sasaki et al. | 252/439 |
| 4,052,332 | 10/1977 | D'Amore et al. | 252/413 |

*Primary Examiner*—P. E. Konopka
*Attorney, Agent, or Firm*—Sughrue, Mion, Zinn, Macpeak and Seas

[57] ABSTRACT

A process for regenerating a deteriorated antimony containing oxide catalyst comprising as essential components of (i) antimony and (ii) at least one metal element selected from the group consisting of iron, cobalt, nickel, manganese, uranium, cerium, tin and copper wherein the antimony containing oxide catalyst is impregnated or sprayed with an aqueous solution of nitric acid and/or a nitrate, and the impregnated catalyst is dried, and then calcined at a temperature in the range of from 400° to 1000° C.

4 Claims, No Drawings

PROCESS FOR REGENERATING AN ANTIMONY CONTAINING OXIDE CATALYST

CROSS REFERENCE TO RELATED APPLICATIONS

This application is a continuation of copending application Ser. No. 959,810, filed Nov. 13, 1978, now abandoned.

BACKGROUND OF THE INVENTION

1. Field of the Invention

This invention relates to a process for regenerating an antimony containing oxide catalyst, and more particularly to a process for regenerating an antimony containing oxide catalyst the activity of which has been deteriorated as a result of its use in the oxidation, ammoxidation or oxidative dehydrogenation of hydrocarbons.

2. Description of the Prior Art

It is well known that a metal oxide compositions comprising as essential components (i) antimony and (ii) at least one metal element selected from the group consisting of iron, cobalt, nickel, manganese, uranium, cerium, tin and copper is useful as a catalyst for the oxidation, ammoxidation or oxidative dehydrogenation of hydrocarbons; for example, it can be advantageously used in the production of unsaturated aldehydes through the oxidation of olefins, the production of unsaturated nitriles through the ammoxidation of olefins, and in the production of diolefins through the oxidative dehydrogenation of olefins. As catalysts for the production of acrylonitrile by the ammoxidation of propylene, Japanese Patent Publication No. 19111/64 discloses a catalyst comprising an oxide of antimony and iron, cobalt or nickel, U.S. Pat. No. 3,152,170 discloses a catalyst comprising an oxide of antimony and tin, U.S. Pat. No. 3,308,151 discloses a catalyst comprising an oxide of antimony and uranium, and U.S. Pat. Nos. 3,200,081 and 3,340,291 disclose a catalyst comprising an oxide of antimony and manganese or copper. Some later improvements on these catalysts are disclosed in U.S. Pat. No. 3,668,147, Japanese Pat. No. 40985/72 and Japanese Patent Publication No. 19764/72 wherein tellurium and at least one element selected from the group consisting of molybdenum, vanadium and tungsten is incorporated in catalysts comprising oxides of antimony and iron, antimony and tin and antimony and uranium, respectively. Japanese Pat. No. 40957/72 describes a catalyst comprising an oxide of antimony and at least one element selected from the group consisting of cerium, titanium, manganese, cobalt, nickel and copper.

In spite of their good catalytic performance, none of the above catalysts are fully satisfactory upon prolonged use and their service life is not always sufficiently long. Even the improved catalysts are subject to a gradual decrease in their activity with extended use and improper reaction conditions often accelerate a reduction in the catalytic activity. It is economically unfeasible to continue using a catalyst which has had its activity reduced below a certain level, however, since catalysts of the above specified type are expensive, it is a substantial expenditure for the manufacturer to replace the deteriorated catalyst with a fresh one. It would therefore be economically advantageous if a practical method for regenerating the catalyst were available.

As will be understood from the above explanation, one criterion for determining whether a catalyst is deteriorated or whether a deteriorated catalyst has been regenerated by a regenerative method is on an economic level, in contrast to a technical level, which takes into account the activity and selectivity of the catalyst. Based on experience a catalyst is "deteriorated" if the yield of the end product is more than 2 to 3% of the yield obtained using the fresh catalyst, and a catalyst is "regenerated" if such yield is restored to the original level or higher.

It is difficult to enumerate the causes of deterioration of a catalyst which occurs during its use. In most cases, many factors combine to cause such deterioration, what is more, locating a particular contributing factor does not directly lead to the development of an effective method of regenerating the catalyst. Therefore, many attempts at providing effective regeneration of the catalyst have turned unsuccessful.

A method of regenerating an antimony-uranium oxide catalyst is described in Japanese patent application (OPI) No. 8615/72 (The term "OPI" as used herein refers to a "published unexamined Japanese patent application".) corresponding in part to British Pat. No. 1,365,096. That method is characterized by heating an antimony-uranium oxide catalyst complex in a fluidized state, in a non-reducing gas at a temperature of from 800° to 1800° F. and for a time such that the surface area of the catalyst does not fall below a minimum critical level of 5 square meters per gram. The basic concept behind the method is to heat the catalyst before its performance, which is determined by the surface area of the catalyst, drops to a minimum critical level. In addition, the method is applicable over a wide range of temperatures. Therefore, this method may be considered a satisfactorily practical method for regenerating the catalyst.

However, antimony containing oxide catalysts wherein antimony is combined with elements other than uranium cannot be regenerated by such simple method. For example, only iron-antimony containing oxide catalysts which has a specific composition can be regenerated and under relatively limited conditions, only when the deteriorated catalyst has a specified nature. Accordingly the method described in Japanese Patent Publication No. 8615/72 is only suitable for regenerating of an antimony-uranium oxide catalyst.

U.S. Pat. No. 4,049,575 discloses a novel process for the production of catalysts that include the catalyst which may be regenerated in accordance with the process of this invention. In accordance with the process disclosed in U.S. Pat. No. 4,049,575 a catalyst composition is prepared by impregnating or spraying onto a mixed metal oxide composition consisting of antimony and a specific metal with a solution containing other active components. The process can be advantageously used in regenerating a deteriorated catalyst, as demonstrated by some of the working examples in the patent, but the method is rather complex and costly because it involves preparing a solution of the catalytic component with which the catalyst is impregnated, impregnating the catalyst with a predetermined amount of the solution, drying, and calcining the impregnated catalyst. In particular, the method requires that the impregnating solution contain at least two catalytically active components, but it is not easy to prepare one stable impregnating solution which does not produce a precipitate, for instance. As a result, it is sometimes necessary to use rather expensive reagents as starting materials of active components. The method also introduces new catalytic components to the catalyst, thus yielding a regenerated catalyst having a different composition and different physical properties than the original catalyst or having a different reaction rate and different optimum reaction conditions. Therefore, it is often difficult to use the catalyst regenerated in this way in combination with the fresh (unregenerated) catalyst without some disadvantage. For these reasons, the method disclosed in U.S. Pat. No. 4,049,575 has not been found entirely satisfactory for regenerating antimony containing oxide catalysts.

SUMMARY OF THE INVENTION

It is therefore the object of this invention to provide a process for regenerating a deteriorated antimony containing oxide catalyst which (i) can be conducted over a wide range of regenerating conditions, (ii) is simple to operate and (iii) has few problems associated with practical use. The antimony containing oxide catalyst which may be regenerated by the process of this invention is useful in the oxidation, the ammoxidation or the oxidative dehydrogenation of hydrocarbons and has had its activity deteriorated with use in these reactions.

This invention achieves this objective by impregnating or spraying onto the deteriorated antimony containing oxide catalyst with an aqueous solution of nitric acid and/or a nitrate followed by calcining the impregnated catalyst at a temperature ranging from 400° to 1000° C.

In summary, this invention provides a process for regenerating an antimony containing oxide catalyst comprising as essential components of (i) antimony and (ii) at least one metal element selected from the group consisting of iron, cobalt, nickel, manganese, uranium, cerium, tin and copper and which has had its activity deteriorated after use in the oxidation, the ammoxidation or the oxidative dehydrogenation of hydrocarbons, wherein the deteriorated antimony containing oxide catalyst is impregnated or sprayed with an aqueous solution of nitric acid and/or a nitrate, dried, and calcined at a temperature in the range from 400° to 1000° C.

DETAILED DESCRIPTION OF THE INVENTION

The catalyst regenerated by the process of this invention is an antimony containing oxide catalyst which has had its activity (expressed in the yield of end product) gradually reduced in the course of the oxidation, the ammoxidation or the oxidative dehydrogenation of hydrocarbons or impaired due to improper operating conditions in such reactions (e.g. in correct feed gas composition or reaction temperature). Of course, the process of this invention is equally useful in regenerating catalysts deteriorated in other reactions, however, these reactions are noted because they are reactions in which the antimony oxide catalysts are frequently employed.

Such antimony containing oxide catalysts comprise as essential components (i) antimony and (ii) at least one metal element selected from the group consisting of iron, cobalt, nickel, manganese, uranium, cerium, tin and copper; it may optionally also contain one or more elements selected from the group consisting of magnesium, calcium, strontium, barium, lanthanum, titanium, zirconium, vanadium, niobium, tantalum, chromium, molybdenum, tungsten, zinc, cadmium, boron, aluminum, gallium, germanium, lead, phosphorus, bismuth, and tellurium.

The composition of the antimony containing oxide catalyst is not particularly limited, but a preferred composition is in the range represented by the following empirical formula:

$$Me_aSb_bX_cR_dQ_eO_f$$

wherein Me is at least one element selected from the group consisting of Fe, Co, Ni, Mn, U, Ce, Sn and Cu; X is at least one element selected from the group consisting of V, Mo, W, Nb and Ta; R is at least one element selected from the group consisting of B, P, Bi and Te; Q is at least one element selected from the group consisting of Mg, Ca, Sr, Ba, La, Ti, Zr, Cr, Zn, Cd, Al, Ga, Ge and Pb; the subscripts a, b, c, d, e and f represent atomic ratios, and where a is 10, b is 5 to 60, c is 0 to 30, preferably 0 to 15, d is 0 to 10, preferably 0 to 5, e is 0 to 20, preferably 0 to 10, and f is the number of oxygen atoms that combine with these components to form an oxide.

Such catalyst compositions may or may not be carried on a carrier. Suitable carriers include silica, alumina, titania, zirconia, silica alumina, etc.

The concentration of aqueous solution of nitric acid and/or a nitrate with which the deteriorated catalyst is impregnated or sprayed onto according to this invention is not particularly limited. A convenient nitric acid solution has a concentration of about 0.1 to 60%, and preferably a concentration from 0.5 to 40%. The nitrate may be one or more of many water soluble nitrates. For example, ammonium nitrate and other nitrates such as nitrates of alkali metals, alkaline earth metals, lanthanum, cerium, chromium, manganese, iron, cobalt, nickel, copper, silver, zinc, aluminum, bismuth or tellurium may be used in the form of the aqueous solution, provided that the added amount of the metal component does not adversely affect the activity of the catalyst. The concentration of the nitrate may vary in a wide range, but a convenient range is from 1 to 200 g/l.

Nitrates such as ammonium nitrate which completely decompose when heated and produce no residual elements can be used without concern for their concentration, but those nitrates which produce residual elements upon thermal decomposition may have an adverse effect on the performance of the catalyst if they are used in an excessive amounts. The extent to which the residual element affects the catalytic activity varies from one element to the next, but broadly stated, the maximum atomic ratio of the element contained in the nitrate to the antimony should be 10 or less: 100 that is the ratio should be <10/100. If this ratio is exceeded, the treated catalyst in many cases will have a different activity than that of the original catalyst, hence the conditions under which the fresh catalyst has been used cannot automatically be used for the regenerated catalyst. The exact proportions of an element contained in the nitrate can be determined on a case-by-case basis because exceeding the ratio defined above may not always pose a problem in practical applications of this invention.

It will be apparent to those skilled in the art that the nitrate salt solution may contain excess nitric acid.

Various methods may be employed for impregnating or spraying the deteriorated catalyst with the aqueous solution of nitric acid and/or nitrate according to this invention. In one example, an aqueous solution of nitric acid and/or a nitrate is prepared in an amount more than enough to immerse the deteriorated catalyst, the catalyst is then held in the solution for a period of time sufficient for the pores in the catalyst to be adequately impregnated with the solution. A period of about 10 minutes to 2 hours generally serves this purpose. Then, the catalyst is separated from the aqueous solution of nitric acid and/or a nitrate, dried and calcined to prepare a regenerated catalyst. Alternatively, a metered amount of the impregnating solution that is corresponding to the pore volume in the catalyst may be adequately mixed with the catalyst. This method is particularly suitable for regenerating a fluid catalyst. Another suitable technique is to spray the impregnating solution onto the catalyst which is placed in, for example, a rotary drum.

No matter what kind of means is used, it is important that the aqueous solution of nitric acid and/or a nitrate reaches every part of the catalyst uniformly. Unlike the method disclosed in U.S. Pat. No. 4,049,575, the method of this invention does not add catalytically active components, and as a result, the performance of the regenerated catalyst is not impaired even if the amount of nitric acid moiety is excessive. The only consideration that is necessary to determine the upper limit of the amount of the nitric acid is the convenience of the practical operation, thus allowing a wide range within which to vary the amount of nitric acid and/or nitrate. It is preferred that the aqueous solution of nitric acid and/or nitrates having the above concentrations be used in an amount ranging from 0.01 to 50% based on the weight of the catalyst to be regenerated.

The significance of the nitric acid and/or the nitrates in the process of this invention is not yet fully understood, but assuming that the deterioration of the antimony containing oxide catalyst is due largely to a partial reduction of the catalyst, it is believed that the nitric acid and/or nitrate, either inherently exhibits a strong oxidizing action which contributes to re-oxidation of the deteriorated catalyst or re-constructs the effective crystalline structure of the catalyst. It is also possible that contact with the aqueous solution of nitric acid and/or the nitrate produces a slight solution of some components of the catalyst on the surface, that may favorably affect regeneration of the catalyst. Therefore, it is highly recommended that the aqueous solution of nitric acid and/or nitrate added to the deteriorated catalyst be subjected to decomposition and calcining without separation from the catalyst.

According to this invention, the catalyst thus impregnated or sprayed with the aqueous solution of nitric acid and/or nitrate is then dried and then calcined at a temperature in the range from 400° to 1000° C., preferably 600° to 900° C. The drying of the impregnated catalyst is carried out at 50° C. to 400° C. The drying time is a time such that the moisture is sufficiently removed at the specified temperature. A calcination temperature lower than 400° C. does not provide adequate regeneration of the catalyst, and a temperature higher than 1000° C. reduces the activity and strength of the catalyst contrary to the intended purpose. If desired, the catalyst may be calcined at a temperature of 300° C. to 600° C. before the final calcination. The preferred calcination temperature varies according to the catalyst but is in the vicinity of or lower than the final or highest calcination temperature used in manufacturing the catalyst. Stated more specifically, the calcination temperature is in a range from a temperature 150° C. less to 20° C. more than the final or highest calcination temperature used in the manufacture of the catalyst. However, temperatures less than 400° C. and more than 1000° C. are not suitable for the reasons already stated.

The calcination time is suitably selected from a range of about 10 minutes to about 10 hours. The calcination temperature used in manufacturing the catalyst varies with the catalyst composition and a preparation method but an approximate calcination temperatures typically used in preparing the catalysts regenerated in accordance with the present invention is a temperature of 500° C. to 1000° C. The calcination temperature range used in manufacturing the antimony containing oxide catalyst in particular may be 600° to 950° C.

A non-reducing atmosphere is preferably used for calcining the catalyst. An air flow is conveniently used for practical purposes, but nitrogen, helium, carbon dioxide gas, etc. may be used.

There is no particular limitation on the type of the apparatus for calcining the deteriorated catalyst according to the process of this invention; a stationary furnace, a tunnel furnace, a rotary kiln, a fluidized bed calciner and other furnaces conventionally used for manufacturing of catalysts can be used for this purpose. The process of this invention can be applied to both fluidized type and fixed bed type antimony containing oxide catalysts.

If the antimony containing oxide catalyst to be treated by the process of this invention is to be used as a fluidized catalyst, it is conveniently and preferably fluidized in a fluidized bed calciner that provides a uniform temperature distribution. As disclosed in Japanese Pat. No. 3756/75 a homogeneous, high-activity fluidized bed catalyst of an antimony containing solid catalyst suitable for use in fluidized bed reaction can be made by calcining catalyst particles at a high temperature (from about 400° to 1100° C.) in a fluidized bed calciner wherein the cross-sectional ratio of area in the upper portion to lower portion of the catalyst packed bed is from 1.2 to 3 and supplying as a fluidizing gas molecular oxygen or a gas that contains molecular oxygen at a linear velocity of 15 cm/sec or more in lower portion and 60 cm/sec or less in upper portion. Generally, the conditions for regeneration of the catalyst may be more broadly specified in comparison with those for the preparation of the catalyst, the regeneration is carried out easily. Therefore, the fluidized bed calciner as described above is not specified as to type and various types can be used. However, it is necessary to charge a fluidizing gas at a linear velocity above the incipient fluidization point. Such a method can be employed in regenerating the deteriorated catalyst according to the method of this invention. The process of this invention can be applied to a fluidized bed catalyst as well as to a fixed bed catalyst.

The catalyst thus regenerated by the process of this invention has its performance (selectivity, activity and optimum reaction conditions) restored to a level substantially equal to that of the fresh catalyst. In addition, the physical properties of the regenerated catalyst are little affected. Accordingly, the regenerated catalyst can be used independently of or in combination with fresh catalyst. As a further advantage, the process of this invention can be operated in a very simple manner and is suitable for regenerating many types of antimony containing oxide catalysts, thus offering great advantages in industrial applications.

The operation and effect of this invention will now be described in greater detail by reference to the following examples and comparative examples which are not intended to limit the scope of this invention.

In this invention, the yield of end product is defined as follows:

Yield of end product (%) =

$$\frac{\text{carbon weight of end product}}{\text{carbon weight of feed hydrocarbon}} \times 100$$

The following conditions were used to test the activity of the catalysts in the Examples and Comparative Examples below.

Testing Condition I

A U-shaped steel tube having an inner diameter of 16 mm was packed with 50 ml of a catalyst and heated in a molten salt bath comprising a mixture of equal weights of sodium nitrite and potassium nitrate. The reactor was fed with a gas of the following composition as a rate of 10 l (STP) per hour. The reaction pressure was atmospheric.

$O_2$ (as air)/propylene = 2.2 (molar ratio)
$NH_3$/propylene = 1.3 (molar ratio)

The temperature of the molten salt bath was sequentially varied, and reaction was continued for several hours at each temperature. The reaction gas was then recovered and subjected to quantitative analysis by gas chromatography.

Testing Condition II

A U-shaped steel tube having an inner diameter of 16 mm was packed with 25 ml of a catalyst and heated in a molten salt bath comprising a mixture of equal weights of sodium nitrite and potassium nitrate. The reactor was fed with a gas of the following composition at 9 l (STP) per hour. The reaction pressure was atmospheric.

$O_2$ (as air)/butene-1 = 1.1 (molar ratio)
water/butene-1 = 1.5 (molar ratio)

Testing Condition III

A U-shaped steel tube having an inner diameter of 16 mm was packed with 25 ml of a catalyst and heated in a molten salt bath comprising a mixture of equal weights of sodium nitrite and potassium nitrate. The reactor was fed with a gas of the following composition at 12 l (STP) per hour. The reaction pressure was atmospheric.

$O_2$ (as air)/isobutene = 3.5 (molar ratio)
$NH_3$/isobutene = 1.3 (molar ratio)
water/isobutene = 4.0 (molar ratio)

Testing Condition IV

A fluidized bed reactor having an inner diameter of 8 inches at the reaction zone was packed with catalyst. The reactor was fed with a gas of the following composition at an apparent linear velocity of 18 cm/sec. The reaction pressure was 0.5 kg/cm²G.

$O_2$ (as air)/propylene = 2.5 (molar ratio)
$NH_3$/propylene = 1.2 (molar ratio)

Testing Condition V

A fluidized bed reactor having an inner diameter of about 55 mm at the reaction zone and which had baffles provided inside for improving contact efficiency was packed with a catalyst.

The reactor was fed with a gas of the following composition at an apparent linear velocity of 13 cm/sec. The reaction pressure was atmospheric.

$O_2$ (as air)/propylene = 2.2 (molar ratio)
$NH_3$/propylene = 1.15 (molar ratio)

EXAMPLE 1

A catalyst having the empirical formula: $Fe_{10}Sb_{25}O_{65}(SiO_2)_{30}$ was obtained as follows. The following reagents were prepared.

Reagent I: A 61 g sample of metal antimony powder (less than 200 mesh) was gradually added to 230 ml of heated nitric acid (specific gravity: 1.38). After all antimony powder was added and a brown gas stopped generating, the mixture was allowed to stand at room temperature for 16 hours. The excess nitric acid was then removed, and the precipitate was washed three times with 100 ml of water.

Reagent II: A sample of 11.2 g of electrolytic iron powder was gradually added to a solution comprising 81 ml of nitric acid (specific gravity: 1.38) and 100 ml of water until a homogeneous solution was obtained.

Reagent III: A 180 g sample of silica sol (containing 20 wt% of $SiO_2$) was weighed out.

Reagents I to III above were mixed and its pH was adjusted to 2.0 by gradually adding 28% aqueous ammonia while stirring. The slurry was dried to a solid by boiling with stirring. The solid mass obtained was crushed and calcined first at 200° C. for 2 hours, then calcined at 400° C. for 2 hours. The calcined product was blended with water and shaped into a cylindrical particles having a diameter of 2 mm and a height of 2 mm. The granules were dried at 130° C. for 16 hours and calcined at 900° C. for 2 hours in air.

The catalyst prepared was subjected to reaction at 420° C. for 10 hours under the above Testing Condition I.

The yield of acrylonitrile was initially 66% and reduced to 63% with 10 hours of reaction.

The deteriorated catalyst was extracted from the reactor and subjected to regenerative treatment according to this invention. The catalyst was immersed in 30% nitric acid until it was deaerated (until no more air bubbles formed) and passed through a glass filter to remove the excess nitric acid. The catalyst thus impregnated with nitric acid was recovered from the filter, dried at 130° C. for 16 hours, calcined first at 200° C. for 2 hours, then at 400° C. for 2 hours and finally at 700° C. for 5 hours.

The regenerated catalyst was subjected to reaction under the same test conditions as used above and acrylonitrile was obtained in 66% yield.

EXAMPLE 2

A catalyst having the empirical formula: $U_{10}Sb_{50}O_{126.7}(SiO_2)_{60}$ was obtained as follows. The following reagents were prepared.

Reagent I: A 60.9 g sample of metal antimony powder (less than 100 mesh) was gradually added to 225 ml of heated nitric acid (specific gravity: 1.38). After the antimony powder was added and a brown gas stopped generating, the mixture was allowed to stand at room temperature for 16 hours. The excess nitric acid was then removed, and the precipitate was washed three times with 100 ml of water.

Reagent II: A 50.2 g sample of uranyl nitrate $UO_2(NO_3)_2.6H_2O$ was dissolved in 100 ml of water.

Reagent III: A 180.3 g sample of silica sol (containing 20 wt% of $SiO_2$) was weighed out.

Reagents (II) and (III) were mixed with Reagent (I) and dried to solid with heat under adequate stirring. The solid mass was crushed and calcined first at 200° C. for 2 hours and then at 400° C. for 2 hours. The calcined product was blended with water and shaped into cylindrical particles having a diameter of 2 mm and a height of 2 mm. The particles were dried at 130° C. for 16 hours and calcined at 850° C. for 3 hours.

The catalyst thus obtained was subjected to reaction at 380° C. for 10 hours under Testing Condition II. The yield of butadiene which was initially 63% but decreased to 60% in the course of the reaction.

The deteriorated catalyst was extracted from the reactor and subjected to regenerative treatment according to this invention as follows. The catalyst was immersed in a 5% solution of ammonium nitrate until it was deaerated (until no more air bubbles were formed), and then passed through a glass filter to remove the excess ammonium nitrate solution. The wet catalyst was dried at 130° C. for 16 hours, and calcined first at 200° C. for 2 hours, then at 400° C. for 2 hours, and finally at 600° C. for 5 hours.

The regenerated catalyst was subjected to reaction under the same test conditions as used above (Test Condition II) and butadiene was obtained in a yield of 64%.

EXAMPLE 3

A catalyst having the empirical formula: $Sn_{10}Sb_{25}O_{70}(SiO_2)_{30}$ was prepared as follows. The following Reagents I and II were prepared.

Reagent I: A mixture of 60.9 g of metallic antimony powder (less than 100 mesh) and 23.7 g of metallic tin powder (less than 100 mesh) was gradually added to 300 ml of heated nitric acid (specific gravity: 1.38). After the brown gas stopped generating, the mixture was allowed to stand at room temperature for 16 hours. The excess nitric acid was then removed and the precipitate was washed three times with 100 ml of water.

Reagent II: A sample of 180.3 g of silica sol (containing 20 wt% of $SiO_2$) was weighed out.

Reagents (I) and (II) were mixed and was dried to a solid with heat under adequate stirring. The solid mass was crushed and calcined first at 200° C. for 2 hours, then at 400° C. for 2 hours. The calcined product was blended with water and shaped into 2 mm high and 2 mm in diameter cylindrical granules. The granules were dried at 130° C. for 16 hours and calcined at 900° C. for 2 hours.

The catalyst obtained was subjected to reaction at 430° C. for 10 hours under Testing Condition III. The yield of methacrylonitrile decreased from an initial value of 43% to 21%.

The deteriorated catalyst was extracted from the reactor and subjected to a regenerative treatment according to this invention. The catalyst was immersed in 10% nitric acid, until it was deaerated (until substantially no more air bubbles were found) and passed through a glass filter to remove the excess nitric acid. The catalyst impregnated with nitric acid was recovered from the glass filter, dried at 130° C. for 16 hours, calcined first at 200° C. for 2 hours, then at 400° C. for 2 hours, and finally at 700° C. for 5 hours.

The regenerated catalyst thus prepared was subjected to reaction under the same test conditions used above (Test Condition III) and methacrylonitrile was obtained in a yield of 45%.

EXAMPLE 4

A catalyst having the empirical formula: $Ce_{10}Sb_{60}W_{0.5}Te_2O_{140.5}(SiO_2)_{30}$ was prepared as follows.

Reagent I: A 60.9 g sample of metallic antimony powder (less than 100 mesh) was gradually added to 225 ml of heated nitric acid (specific gravity: 1.38). After all the antimony powder was added and the brown gas stopped generating, the mixture was allowed to stand at room temperature for 16 hours. The excess nitric acid was removed and the precipitate was washed three times with 100 ml of water.

Reagent II: A 46.5 g sample of ammonium cerium nitrate $Ce(NO_3)_2.2NH_4.NO_3.4H_2O$ was dissolved in 100 ml of water.

Reagent III: A 3.8 g sample of telluric acid $H_6TeO_6$ was dissolved in 50 ml of water.

Reagent IV: A 0.83 g of ammonium paratungstate was dissolved in 50 ml of water.

Reagent V: A 75.1 g of silica sol (containing 20 wt% of $SiO_2$) was weighed out.

A mixture of Reagents II and IV was mixed sequentially with Reagents III, V and I, and dried to a solid by heating under adequate stirring. The solid mass was crushed and calcined first at 200° C. for 2 hours, then at 400° C. for 2 hours. The calcined product was blended with water and shaped into a cylindrical granules having a diameter of 2 mm and a height of 2 mm. The granules were dried at 130° C. for 16 hours and calcined at 800° C. for 5 hours.

The catalyst prepared was subjected to reaction at 440° C. for 22 hours under Testing Condition I. The yield of acrylonitrile was reduced from an initial 67% to 65% in the course of the reaction.

The deteriorated catalyst was extracted from the reactor and subjected to regenerative treatment according to this invention. The catalyst was immersed in a 10 g/l iron nitrate solution until it was deaerated and passed through a glass filter to remove the excess iron nitrate solution. The wet catalyst was dried at 130° C. for 16 hours, calcined first at 200° C. for 2 hours, then at 400° C. for 2 hours, and finally at 750° C. for 4 hours.

The regenerated catalyst was subjected to reaction under the same test conditions (Condition I) as used above, and acrylonitrile was produced in a yield of 67%.

EXAMPLE 5

A catalyst having the empirical formula: $Cu_{0.5}Mo_{0.25}Te_{1.0}Fe_{10}Sb_{25}O_{68}(SiO_2)_{60}$ was prepared in the following manner.

Reagent I: A 5.82 kg powder of antimony trioxide (of a particle size less than 20μ) was weighed out.

Reagent II: A 0.894 kg sample of electrolytic iron powder was weighed out. A 6.4 l sample of nitric acid (specific gravity: 1.38) was mixed with 4 l of water and heated. The iron powder was gradually added to the mixture to put it into solution.

Reagent III: A 70.6 g sample of ammonium paramolybdate, and 184 g of telluric acid was dissolved in one liter of water.

Reagent IV: A sample of 9.61 kg of silica sol (containing 30 wt% of $SiO_2$) was weighed out.

Reagent V: A 194 g sample of copper nitrate was dissolved in one liter of water.

Reagents (I) to (V) were mixed and the pH of the mixture was adjusted to 2.0 with 15% aqueous ammonia under adequate stirring, and heated at 100° C. for 4 hours with adequate stirring.

The slurry thus obtained was spray dried in a conventional manner. The fine spherical particles thus produced were calcined first at 250° C. for 2 hours, then at 400° C. for 2 hours, and finally at 810° C. for 4 hours.

The catalyst thus prepared was subjected to reaction at 440° C. for 800 hours under Testing Condition IV. The yield of acrylonitrile was initially 70% and reduced to 66%.

The deteriorated catalyst was extracted from the reactor and divided into 10 portions each weighing 1.2 kg for regeneration according to this invention. As the impregnating solution, an aqueous nitric acid or nitrate solution was prepared in an amount equal to the volume of pores (0.35 ml/g), and mixed with the deteriorated catalyst until the pores were thoroughly impregnated with the solution.

The following impregnating solutions were used.

|    | solution          | concentration |
|----|-------------------|---------------|
| 5A | manganese nitrate | 4.8 g/l       |
| 5B | silver nitrate    | 1.4 g/l       |
| 5C | zinc nitrate      | 7.5 g/l       |
| 5D | aluminum nitrate  | 9.5 g/l       |
| 5E | bismuth nitrate   | 6.3 g/l       |
| 5F | tellurium nitrate | 1.1 g/l       |
| 5G | nitric acid       | 10%           |

The solution 5E, bismuth nitrate was dissolved in 60% nitric acid. For solution 5F, metallic tellurium powder was oxidized and dissolved in heated 30% nitric acid.

These catalysts were subjected to activity test under Testing Condition V.

Table 1 shows the conditions for regeneration and the results of the activity test on each of the regenerated catalysts. It is quite clear that the activity of the catalysts was restored to a satisfactory level.

COMPARATIVE EXAMPLE 1

Each of the deteriorated catalysts obtained in Example 5 was calcined in air under the following conditions.
(1) 650° C. for 4 hours
(2) 700° C. for 4 hours
(3) 750° C. for 4 hours The catalysts were then tested for their activity under Testing Condition V. The results are shown in Table 1.

EXAMPLE 6

A catalyst of the empirical formula:
$W_{0.5}Te_{1.0}Co_{3.0}Fe_{10}Sb_{25}O_{72}(SiO_2)_{60}$ was prepared by repeating the procedures of Example 5, except that the tungsten and cobalt components were employed as ammonium paratungstate and cobalt nitrate in amounts of 208 g and 1.395 kg respectively. The final calcination step was for 5 hours at 790° C.

As the catalyst was being subjected to reaction at 450° C. under Testing Condition V, the air flow dropped sharply due to a misoperation. The nomal reaction conditions were soon restored, but the yield of acrylonitrile was reduced. Then, the yield of acrylonitrile which was initially 79.1% dropped to 72.4% as the results of the activity test under Testing Condition V of the catalyst before or after deteriorating used in the reactions.

The deteriorated catalyst was extracted from the reactor and subjected to regenerative treatment according to the method of Example 5.

The following impregnating solutions were used.

|    | solution                                       | concentration |
|----|------------------------------------------------|---------------|
| 6A | nitric acid                                    | 7%            |
| 6B | cobalt nitrate                                 | 13.0 g/l      |
| 6C | nitric acid + telluric acid                    | 24.6 g/l      |
| 6D | tellurium (dissolved in 40% nitric acid) +     | 11.4 g/l      |
|    | copper nitrate                                 | 26.4 g/l      |

Table 1 shows the conditions for regeneration and the result of the activity test on the regenerated catalysts. It is clear that the activity of the catalysts was restored to a satisfactory level.

COMPARATIVE EXAMPLE 2

The deteriorated catalyst obtained in Example 6 was regenerated by the method described in U.S. Pat. No. 4,049,575.

Ammonium paratungstate was dissolved in water in an amount of 37.4 g/l. Metallic tellurium powder was oxidized with nitric acid to prepare a solution of 36.4 g/l tellurium nitrate. The two solutions were mixed at an atomic ratio of 1:2 (tungsten to tellurium), whereupon a precipitate was formed. Accordingly instead of using a solution to tellurium nitrate an aqueous solution of telluric acid (65.6 g/l) was used as the tellurium component and mixed with an aqueous solution of ammonium paratungstate. The thus prepared solution was used to impregnate the deteriorated catalyst, which was then calcined at 720° C. for 4 hours. The catalyst had the composition: $W_{0.7}Te_{1.4}Co_{3.0}Fe_{10}Sb_{25}O_{72}(SiO_2)_{60}$.

The catalyst was subjected to activity test under Testing Condition V. The result is shown in Table 1.

EXAMPLE 7

A catalyst of the empirical formula:
$W_{0.5}Te_{1.5}Ni_1Mn_1Fe_{10}Sb_{25}O_{72.5}(SiO_2)_{50}$ was prepared by repeating the procedure of Example 5, except that 208.5 g ammonium paratungstate, 464.5 g nickel nitrate and 458.5 g manganese nitrate were employed as the starting material of the tungsten nickel and manganese components. The final calcination was for 4 hours at 780° C.

The catalyst was subjected to reaction at 460° C. under Testing Condition V, producing acrylonitrile in a yield of 76.8%. As the reaction temperature was increased to 480° C., the concentration of oxygen at the outlet decreased to almost zero, accompanied with a decrease in the yield. Then, the initial temperature 460° C. was restored, but the yield of acrylonitrile had dropped to 70.1%.

The deteriorated catalyst was extracted from the reactor and subjected to regenerative treatment according to the method of this invention. The procedure of impregnation was the same as that used in Example 5.

The following impregnating solutions were used.

|    | solution       | concentration |
|----|----------------|---------------|
| 7A | copper nitrate | 26.8 g/l      |
| 7B | iron nitrate   | 36.7 g/l      |
| 7C | nitric acid    | 5%            |

Table 2 shows the conditions for regeneration and the result of activity test on the regenerated catalysts.

COMPARATIVE EXAMPLE 3

The deteriorated catalyst obtained in Example 7 was calcined at 720° C. for 4 hours in air. Activity tests were carried out as described above under Testing Condition V. Table 2 shows the result of the activity test on the calcined catalyst.

TABLE 1

| Catalyst/Example | Impregnating Solution | Atomic Ratio of Me per 100 of Sb | Final Calcination Temperature (°C.) | Final Calcination Time (hrs) | Reaction Temperature (°C.) | Yield of Acrylonitrile (%) |
|---|---|---|---|---|---|---|
| Example 5 before deterioration | | | 810 | 4 | 460 | 77.6 |
| after deterioration | | | — | — | 460 | 74.8 |
| | 5-A | Mn 0.2 | 750 | 4 | 460 | 77.0 |
| | 5-B | Ag 0.1 | 720 | 5 | 460 | 77.5 |
| | 5-C | Zn 0.3 | 700 | 5 | 460 | 78.0 |
| | 5-D | Al 0.3 | 700 | 5 | 460 | 77.8 |
| | 5-E | Bi 0.2 | 700 | 5 | 460 | 76.9 |
| | 5-F | Te 0.1 | 650 | 4 | 460 | 77.2 |
| | | | 700 | 4 | 460 | 78.1 |
| | | | 750 | 4 | 460 | 77.8 |
| | 5-G | — | 650 | 4 | 460 | 77.8 |
| | | | 700 | 4 | 460 | 77.5 |
| | | | 750 | 4 | 460 | 77.8 |
| Comparative Ex. 1 | — | | 650 | 4 | 460 | 72.6 |
| | — | | 700 | 4 | 460 | 75.3 |
| | — | | 750 | 4 | 460 | 75.8 |
| Example 6 before deterioration | | | 790 | 5 | 450 | 79.1 |
| after deterioration | | | — | — | 450 | 72.4 |
| | 6-A | — | 700 | 3 | 450 | 78.6 |
| | 6-B | Co 0.5 | 750 | 3 | 450 | 79.2 |
| | 6-C | Te 1.2 | 700 | 4 | 450 | 79.7 |
| | 6-D | Te 1.0 Cu 1.0 | 720 | 4 | 450 | 79.5 |
| Comparative Ex. 2 | ammonium tungstate + telluric acid | W 0.8 Te 1.6 | 720 | 4 | 450 | 78.0 |
| | | | | | 440 | 78.5 |

TABLE 2

| Catalyst/Example | Impregnating Solution | Atomic Ratio of Me per 100 of Sb | Final Calcination Temperature (°C.) | Final Calcination Time (hrs) | Reaction Temperature (°C.) | Yield of Acrylonitrile (%) |
|---|---|---|---|---|---|---|
| Example 7 before deterioration | | | 780 | 4 | 460 | 76.8 |
| after deterioration | | | — | — | 460 | 70.1 |
| | 7-A | 0.8 | 720 | 4 | 460 | 76.5 |
| | 7-B | 0.8 | 720 | 4 | 460 | 77.1 |
| | 7-C | — | 720 | 4 | 460 | 76.9 |
| Comparative Ex. 3 | — | | 720 | 4 | 460 | 69.3 |

While the invention has been described in detail and with reference to specific embodiments thereof, it will be apparent to one skilled in the art that various changes and modifications can be made therein without departing from the spirit and scope thereof.

What is claimed is:

1. The process for regenerating a deteriorated antimony containing oxide catalyst consisting essentially of (i) antimony and (ii) at least one metal element selected from the group consisting of iron, cobalt, nickel, manganese, uranium, cerium, tin and copper which consists essentially of the steps of impregnating or spraying said antimony containing oxide catalyst with an aqueous solution of nitric acid, a nitrate solution or a mixture of said nitric acid aqueous solution and said nitrate solution, said nitrate solution being a solution of at least one nitrate selected from the group consisting of ammonium nitrate, an alkali metal nitrate, an alkaline earth metal nitrate and a nitrate of at least one element selected from the group consisting of lanthanum, cerium, chromium, manganese, iron, cobalt, nickel, copper, silver, zinc, aluminum, bismuth and tellurium, drying the thus impregnated catalyst, and calcining the catalyst at a temperature in the range of from 400° to 1000° C.

2. A process for regenerating a deteriorated antimony containing oxide catalyst consisting essentially of (i) antimony, (ii) at least one metal element selected from the group consisting of iron, cobalt, nickel, manganese, uranium, cerium, tin and copper, and (iii) at least one element selected from the group consisting of magnesium, calcium, strontium, barium, lanthanum, titanium, zirconium, vanadium, niobium, tantalum, chromium, molybdenum, tungsten, zinc, cadmium, boron, aluminum, gallium, germanium, lead, phosphorus, bismuth and tellurium which consists essentially of the steps of impregnating or spraying said antimony containing oxide catalyst with an aqueous solution of nitric acid, a nitrate solution or a mixture of said nitric acid solution and said nitrate solution, said nitrate solution being a solution of at least one nitrate selected from the group consisting of ammonium nitrate, an alkali metal nitrate, and alkaline earth metal nitrate and a nitrate of at least one element selected from the group consisting of lanthanum, cerium, chromium, manganese, iron, cobalt, nickel, copper, silver, zinc, aluminum, bismuth and tellurium, drying the thus impregnated catalyst, and calcining the catalyst at a temperature in the range of from 400° to 1000° C.

3. A process according to claim 1 or 2 wherein said calcination temperature is in the vicinity of or lower than the final or highest calcination temperature used in manufacturing the catalyst.

4. A process according to claim 1 or 2, wherein said aqueous solution of nitric acid and/or nitrate solution is an aqueous solution of nitric acid.

* * * * *